US00PP35416P2

(12) United States Plant Patent
Krebs

(10) Patent No.: US PP35,416 P2
(45) Date of Patent: Oct. 10, 2023

(54) ***RHODODENDRON* PLANT NAMED 'HOLDENRHODO221'**

(50) Latin Name: *Rhododendron hybrida*
Varietal Denomination: HoldenRhodo221

(71) Applicant: Holden Forests and Gardens, Kirtland, OH (US)

(72) Inventor: Stephen Krebs, Painesville, OH (US)

(73) Assignee: HOLDEN FORESTS AND GARDENS, Kirtland, OH (US)

( * ) Notice: Subject to any disclaimer, the term of this patent is extended or adjusted under 35 U.S.C. 154(b) by 0 days.

(21) Appl. No.: 18/107,080

(22) Filed: Feb. 9, 2023

(51) Int. Cl.
*A01H 5/02* (2018.01)
*A01H 6/36* (2018.01)

(52) U.S. Cl.
USPC ..... Plt./240
CPC ..... *A01H 6/364* (2018.05)

(58) Field of Classification Search
USPC ..... Plt./240
CPC ..... A01H 6/364; A01H 5/02
See application file for complete search history.

*Primary Examiner* — Keith O. Robinson
(74) *Attorney, Agent, or Firm* — Penny J. Aguirre

(57) ABSTRACT

A new cultivar of hybrid *Rhododendron* plant named 'HoldenRhodo221' that is characterized by its resistance to root rot caused by *Phytophthora cinnamomi,* its cold hardiness (plant and flower buds) at least to U.S.D.A. Zone 5a, its flowers that are red to dark pink in color with strong marginal undulation, its profuse and consistent flowering, its compact plant habit, its foliage that is dark in color and glossy, and its good growth in full sun in unamended sand and gravel loam soils, up to at least pH 6.2.

2 Drawing Sheets

Botanical classification: *Rhododendron hybrida.*
Cultivar designation: 'HoldenRhodo221'.

BACKGROUND OF THE INVENTION

The present invention relates to a new and distinct cultivar of *Rhododendron* plant of hybrid origin, botanically known as *Rhododendron* 'HoldenRhodo221' and will be referred to hereafter by its cultivar name, 'HoldenRhodo221'. 'HoldenRhodo221' is a new cultivar of *Rhododendron* shrub grown for use as a landscape plant.

The new cultivar arose from a controlled breeding program by the Inventor in Madison, Ohio with the goal of developing new cultivars of *Rhododendron* with good resistance to root rot caused by *Phytophthora cinnamomi,* cold hardiness (plant and flower buds), and compact growth habits with diversity in flower forms and colors.

The new cultivar was derived from a cross made by the Inventor in May of 2003 between *Rhododendron* 'Ingrid Mehlquist' (not patented) as the female parent, and *Rhododendron* 'Pride's Early Red' (not patented) as the male parent. The Inventor selected 'HoldenRhodo221' as a single unique plant amongst the seedlings that resulted from the above cross in May of 2010.

Asexual propagation of the new cultivar was first accomplished by semi-hardwood stem cuttings in Madison, Ohio, in fall of 2010 by the Inventor. Asexual propagation by semi-hardwood stem cuttings and tissue culture utilizing meristematic tissue has determined that the characteristics of the new cultivar are stable and are reproduced true to type in successive generations.

SUMMARY OF THE INVENTION

The following traits have been repeatedly observed and represent the characteristics 'HoldenRhodo221'. These attributes in combination distinguish 'HoldenRhodo221' as a new and distinct cultivar of *Rhododendron.*

1. 'HoldenRhodo221' exhibits resistance to root rot caused by *Phytophthora cinnamomi.*
2. 'HoldenRhodo221' exhibits cold hardiness (plant and flower buds) at least to U.S.D.A. Zone 5a.
3. 'HoldenRhodo221' exhibits flowers that are red to dark pink in color with strong marginal undulation.
4. 'HoldenRhodo221' exhibits profuse and consistent flowering.
5. 'HoldenRhodo221' exhibits a compact plant habit.
6. 'HoldenRhodo221' exhibits foliage that is dark in color and glossy.
7. 'HoldenRhodo221' exhibits good growth in full sun in unamended sand and gravel loam soils, up to at least pH 6.2.

The female parent of 'HoldenRhodo221' differs from 'HoldenRhodo221' in having inflorescences that are smaller in size, flower buds that are pink in color and change to white as the flowers open, leaves that are darker in color, lower leaf surfaces that are densely covered with brown colored indumentum, and flowers that do not produce anthers. The male parent of 'HoldenRhodo221' differs from 'HoldenRhodo221' in having greater susceptibility to root rot caused by *Phytophthora cinnamomi,* a less compact plant habit, flowers with margins that lack undulations, and an earlier blooming period. 'HoldenRhodo221' can also be most closely compared to the *Rhododendron* cultivars 'Nova Zembla' (not patented) and 'Holden' (not patented). 'Nova Zembla' is similar to 'HoldenRhodo221' in having red to dark pink colored flowers and in being cold hardy to U.S.D.A. Zone 5. 'Nova Zembla' differs from 'HoldenRhodo221' in having flowers that are less red in color, a less compact plant habit, leaves that are more twisted, and more susceptibility to root rot caused by *Phy-*

*tophthora cinnamomi.* 'Holden' is similar to 'HoldenRhodo221' in having a compact plant habit and in being cold hardy to U.S.D.A. Zone 5. 'Holden' differs from 'HoldenRhodo221' in having flowers that are more pink in color with a more prominent nectar guide on the dorsal petal, more susceptibility to root rot caused by *Phytophthora cinnamomi,* and plant and flower bud cold hardiness to U.S.D.A. Zone 5b but not 5a.

BRIEF DESCRIPTION OF THE DRAWINGS

The accompanying color photographs illustrate the overall appearance and distinct characteristics of the new *Rhododendron.* The plant in the photograph is 6 years in age as grown outdoors in Madison, Ohio.

The photograph in FIG. 1 provides a view of the plant habit of 'HoldenRhodo221' in bloom.

Figure 1:
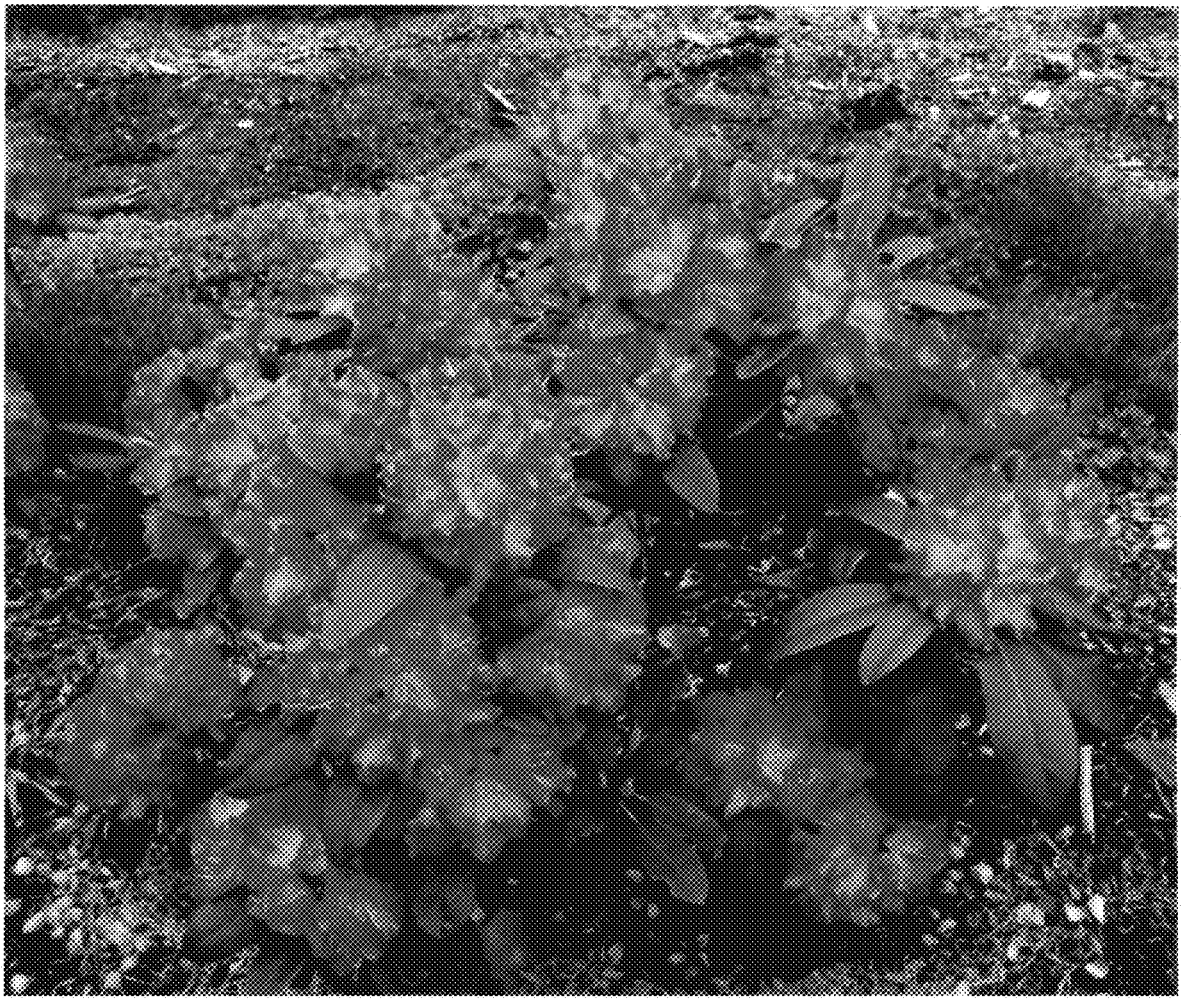
Figure 2:
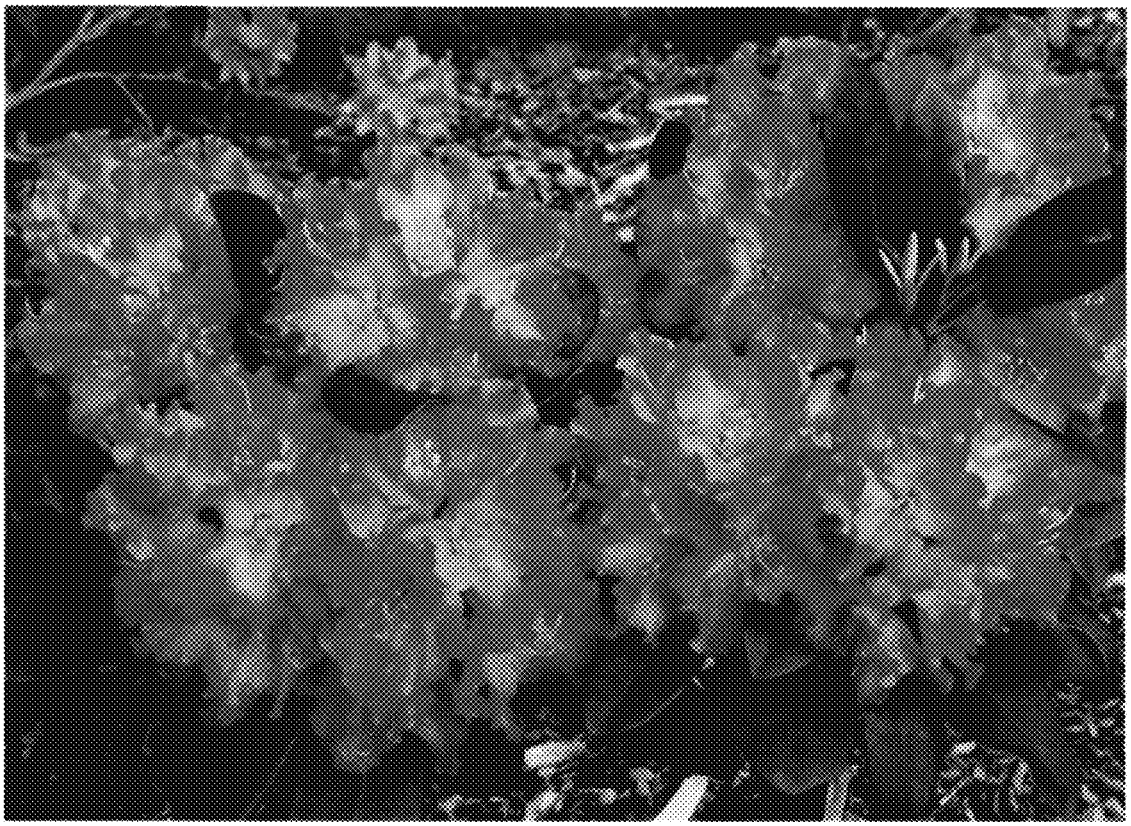

The photograph in FIG. 2 provides a close-up view of the inflorescences of 'HoldenRhodo221'.

The colors in the photographs are as close as possible with the digital photography and printing techniques utilized and the color codes in the detailed botanical description accurately describe the new *Rhododendron.*

DETAILED BOTANICAL DESCRIPTION OF THE PLANT

The following is a detailed description of 11-year-old plants of the new cultivar as grown outdoors in an evaluation garden in Madison, Ohio. The phenotype of the new cultivar may vary with variations in environmental, climatic, and cultural conditions, as it has not been tested under all possible environmental conditions. The color determination is in accordance with The 1995 Colour Chart of The Royal Horticultural Society, London, England, except where general color terms of ordinary dictionary significance are used.

General characteristics:

*Blooming period.*—2 to 3 weeks, weather dependent, typically in mid-late May in Madison, Ohio.

*Plant type.*—Evergreen shrub.

*Plant habit.*—Rounded, compact, and densely branched.

*Height and spread.*—Reaches 52 m in height and 60 cm in width after 11 years in the landscape.

*Cold hardiness.*—Plant is hardy to at least U.S.D.A. Zone 5a, flower buds are resistant to cold damage when exposed to temperatures of −15 F, possibly colder.

*Diseases and pests.*—Observed to be resistant to root rot caused by *Phytophthora cinnamomi* under field conditions, no resistance or susceptibility to pests and other diseases has been observed.

*Root description.*—Fibrous and near 165A in color.

*Propagation.*—Tissue culture (preferred) or semi-hardwood stem cuttings.

*Growth rate.*—Moderate.

*Root development.*—8 to 10 weeks for root initiation and 2 years to produce a plant with flower buds from a rooted cutting in a one-gallon container.

Stem description:

*Shape.*—Rounded.

*Stem color.*—Young, new growth; 143C, mature; 144B, old stems and wood; 164B and 165C, striations of 199A, 199C, 199D, and 201D.

*Stem size.*—Main trunk; 27 cm in height, 3.5 cm in width (2 cm from soil level), lateral stems; 35.7 cm in length, 1.3 cm in width, current season growth; average of 7 cm in length and 5 mm in width.

*Stem surface.*—Young; is slightly rough to the touch, lightly pubescent with hairs an average of 1 mm in length, 158D in color, mature stems become glabrous, older stems and wood; somewhat rough, dull, glabrous, and occasionally exfoliating.

*Stem aspect.*—Stems emerge from plant at various angles, typically approximately 45° from main stem.

*Stem strength.*—Strong.

*Branching.*—Densely branched.

Foliage description:

*Leaf shape.*—Elliptic to obovate.

*Leaf division.*—Simple.

*Leaf base.*—Cuneate.

*Leaf apex.*—Ovate to slightly acute.

*Leaf venation.*—Pinnate, upper surface midrib; 144B in color with lateral vein color matching or nearly matching midrib coloration, lower surface midrib; 145C, lateral veins near 145B.

*Leaf margins.*—Entire with strong undulation.

*Leaf attachment.*—Petiolate.

*Leaf arrangement.*—Alternate to nearly whorled.

*Leaf internode length.*—Ranges from 1 mm to 7.3 cm becoming progressively smaller from base to apex of shoot, 1 mm to 2 mm in whorl of foliage at shoot apex.

*Leaf orientation.*—Held mostly parallel to the ground, some angled 30° above or below parallel.

*Leaf aspect.*—Usually flat but occasionally leaves cup downward.

*Leaf surface.*—Upper surface; smooth, glabrous, lustrous with a thick texture, moderately covered with hairs, <1 mm in length and 159B in color, lower surface; smooth, dull, and glabrous except prominent mid-rib with occasional short cilia <0.5 mm in length.

*Leaf color.*—Young leaves upper surface; 137B in color, young leaves lower surface; a blend of 145A and 146D, mature leaves upper surface; nearest 139A, lower surface 146B.

*Leaf size.*—Ranging between 7 cm to 12.5 cm in length and 2.3 cm to 5.0 cm in width.

*Leaf quantity.*—An average of 9 leaves per current season shoot.

*Petioles.*—Average of 2.5 cm in length and 3 mm in width, 144B in color, smooth texture.

Flower description:

*Inflorescence type.*—Raceme.

*Lastingness of flowers.*—Individual flowers last several days, total duration of bloom ranges from 2 to 3 weeks, self-cleaning.

*Inflorescence size.*—Average of 7.5 cm in height and 11.2 cm in width.

*Flower size.*—An average of 3.8 cm in depth and 6.4 cm in width.

*Flower fragrance.*—Not noticeably fragrant.

*Flower shape.*—Broad, with partially fused corolla.

*Flower number.*—Ranges from 11 to 23 per inflorescence.

*Flower aspect.*—Outward.

*Flower bud.*—Resting (winter buds); typically 1 per terminal branch (can be none or more than one), an average of 1.3 cm in length and 6 mm in diameter as a resting bud, 145A in color with margins and ridges a blend of 175A and 176A, balloon stage; obovate to elliptic in shape, round in cross-section, pointed apex, 2.5 cm in length and diameter, 54A in color at base and a blend of 53A and 60A near terminal end.

*Flower attachment*.—Pedicellate.

*Petal number*.—5, partially fused.

*Petal shape*.—Ovate to elliptic.

*Petal color*.—Opening and fully open upper surface; margins 63A, center 63D, speckled with 66C around nectar guides, fading; margins 66D, center a blend of 63A to 63B, opening and fully open lower surface; margins 63A, center 63B to 63C, speckled with 66C around nectar guides, fading; a blend of 63A to 63B and 65A.

*Petal surface*.—Both surfaces smooth and glabrous.

*Petal margins*.—Inconsistently crenate, undulate.

*Petal apex*.—Acuminate to obtuse, often recurved and keeled.

*Petal base*.—Fused.

*Petal size*.—An average of 4.4 cm in length, 3.2 cm in width.

*Sepal number*.—5.

*Sepal margin*.—Entire.

*Sepal size*.—Average of 1 mm in length and width.

*Sepal apex*.—Rounded to flat.

*Sepal base*.—Fused.

*Sepal color*.—143C.

*Calyx*.—Shallowly cup-shaped an average of 1 mm in length and diameter, with individual sepals separated by rounded sinuses.

*Peduncle*.—An average of 3.2 cm in height and 6 mm in diameter, 144B in color.

*Pedicels*.—An average of 2.2 cm in length 2 mm in diameter, 144B in color, surface is glabrous to slightly pubescent.

Reproductive organs:

*Gynoecium*.—1 Pistil, stigma; round in shape, 59A in color, 1 to 2 mm in diameter, style average 3.4 cm in length, ovary 73D in color.

*Androecium*.—Stamens; typically 10 to 11, anthers; oblong to elliptic in shape, average of 2.5 mm in length, 1 mm in width, 4B in color, filaments; average of 1.9 cm in length, 63C in color, covered in fine white hairs especially near base; pollen present but too small to measure.

*Fruit/seeds*.—Dehiscent, 5 to 6 valved capsule, varying in length and width depending on pollination, color; 165A and 166A with some overtones of 201A in late summer, tends to produce low amounts of seed as a female parent and seed measurements are unavailable.

It is claimed:

1. A new and distinct cultivar of *Rhododendron* plant named 'HoldenRhodo221' as herein illustrated and described.

* * * * *